(12) United States Patent
Yasumura et al.

(10) Patent No.: US 8,222,428 B2
(45) Date of Patent: Jul. 17, 2012

(54) METHOD FOR CONTINUOUSLY PRODUCING OXIDIZED CYCLIC PHENOL SULFIDES

(75) Inventors: Masateru Yasumura, Ibaraki (JP); Yoshikazu Aoki, Fukushima (JP); Masami Ito, Ibaraki (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 218 days.

(21) Appl. No.: 12/867,207

(22) PCT Filed: Feb. 16, 2009

(86) PCT No.: PCT/JP2009/052545
§ 371 (c)(1),
(2), (4) Date: Aug. 11, 2010

(87) PCT Pub. No.: WO2009/102057
PCT Pub. Date: Aug. 20, 2009

(65) Prior Publication Data
US 2011/0028737 A1 Feb. 3, 2011

(30) Foreign Application Priority Data
Feb. 14, 2008 (JP) ................. 2008-032671

(51) Int. Cl.
*C07D 341/00* (2006.01)
(52) U.S. Cl. ........................................... 549/1
(58) Field of Classification Search .................. 549/1
See application file for complete search history.

(56) References Cited

U.S. PATENT DOCUMENTS

| 4,849,138 | A | 7/1989 | Onoe et al. |
|---|---|---|---|
| 5,416,234 | A | 5/1995 | Meier et al. |
| 5,508,416 | A | 4/1996 | Kagano et al. |
| 5,672,751 | A | 9/1997 | Kagano et al. |
| 5,744,609 | A | 4/1998 | Kagano et al. |
| 5,824,808 | A | 10/1998 | Hori et al. |
| 5,998,631 | A | 12/1999 | Kumagai et al. |
| 7,709,172 | B2 | 5/2010 | Yasumura et al. |
| 2009/0042120 | A1 | 2/2009 | Yasumura et al. |
| 2009/0239169 | A1 | 9/2009 | Yasumura et al. |

FOREIGN PATENT DOCUMENTS

| EP | 2011793 A1 | 1/2009 |
|---|---|---|
| JP | 01-040457 A | 2/1989 |
| JP | 06-500119 A | 1/1994 |
| JP | 07-010829 A | 1/1995 |
| JP | 07-145143 A | 6/1995 |
| JP | 09-227553 A | 9/1997 |
| JP | 09-291088 A | 11/1997 |
| JP | 10-081680 A | 3/1998 |
| JP | 10-081681 A | 3/1998 |
| JP | 11-049770 A | 2/1999 |
| JP | 2000-273096 A | 10/2000 |
| JP | 2002-193963 A | 7/2002 |
| JP | 2002-255961 A | 9/2002 |
| WO | 98-09959 A1 | 3/1998 |
| WO | 2007-119797 A1 | 10/2007 |

OTHER PUBLICATIONS

Iki et al., "Selective Oxidation of Thiacalix[4]arenes to the Sulfinyl- and Sulfonylcalix[4]arenes and Their Coordination Ability to Metal Ions", Tetrahedron Letters, 39:7559-7562 (1998).
Morohashi et al., "Selective oxidation of thiacalix[4]arenes to the sulfinyl and sulfonyl counterparts and their complexation abilities toward metal ions as studied by solvent extraction", Tetrahedron, 57:5557-5563 (2001).
Mislin et al., "Sulfone-calixarenes: a new class of molecular building block", J. Chem. Soc., Chem Commun., 13:1345-1346 (1998).
Kumagai et al., "Facile Synthesis of p-tert-Butylthiacalix[4]arene by the Reaction of p-tert-Butylphenol with Elemental Sulfur in the Presence of a Base", Tetrahedron Letters, 38(22):3971-3972 (1997).
Komatsu et al., "Homooxacalix[n]thiophenes: Their one-pot serial synthesis and X-ray structures", Tetrahedron Letters, 40:3749-3752 (1999).
International Search Report for PCT/JP2009/052545, dated Apr. 17, 2009.
International Written Opinion for PCT/JP2009/052545, dated Apr. 17, 2009.

*Primary Examiner* — Taofiq A Solola
(74) *Attorney, Agent, or Firm* — Hoffmann & Baron, LLP

(57) ABSTRACT

The present invention discloses a method for continuously producing an oxidized cyclic phenol sulfide which comprises the continuous steps of reacting a para-alkyl phenol compound as a raw material with 1.7 to 2.5 molar equivalent of sulfur and 0.25 to 0.75 molar equivalent of an alkali metal reagent per 1 mol of the phenol compound (the first step); and oxidizing a cyclic phenol sulfide of the formula (2) produced by the above reaction with an oxidizing agent(s) in the same reactor as that of the first step and without taking the cyclic phenol sulfide out of the reactor:

(2)

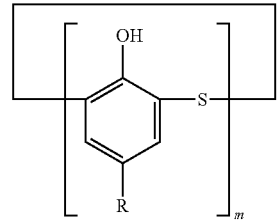

wherein R represents a straight or branched alkyl group having 1 to 6 carbon atoms, and m is an integer from 4 to 8, to obtain an oxidized cyclic phenl sulfide of the formula (3) (the second step):

(3)

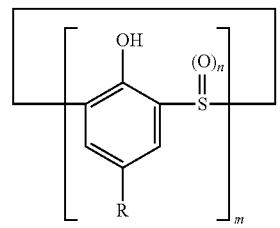

wherein R represents a straight or branched alkyl group having 1 to 6 carbon atoms, m is an integer from 4 to 8, and n is 1 or 2.

14 Claims, No Drawings

METHOD FOR CONTINUOUSLY PRODUCING OXIDIZED CYCLIC PHENOL SULFIDES

CROSS-REFERENCE TO RELATED APPLICATIONS

This application is the National Stage of International Application No. PCT/JP2009/052545, which designates the U.S., filed Feb. 16, 2009 which claims the benefit of Japanese Application No. 2008-032671, filed Feb. 14, 2008, the contents of which are incorporated by reference herein.

TECHNICAL FIELD OF THE INVENTION

The present invention relates to methods for continuously producing oxidized cyclic phenol sulfides, which are useful as metal capture agents or solidifying agents wherein the metal-ion capturing ability thereof is used; optical sensors, ion sensors or substrate specific sensors wherein the recognizing ability of ions or molecules is used; materials for separation membranes and intermediates thereof; charge control agents; catalysts, and the like.

BACKGROUND OF THE INVENTION

Until now, the method comprising the step of oxidizing a corresponding cyclic phenol sulfide is known as the method for producing an oxidized cyclic phenol sulfide. Examples of oxidizing agents used for oxidation reaction include hydrogen peroxide, organic peroxides, peracids, halogen oxides, N-halogen compounds, halogen molecules, oxygen, ozone, a nitric acid, and inorganic oxides. Hydrogen peroxide, halogen molecules, and inorganic oxides such as sodium perborate are preferable among them. Though a preferable solvent varies depending on the kind of an oxidizing agent, it is proposed to use halogenated hydrocarbon solvents such as chloroform and dichloromethane; alcohols such as methanol and ethanol; acetonitrile; polar solvents such as an acetic acid and water, and the like. Further, it is also known that, if necessary, catalysts such as vanadium (V) oxide, sodium metavanadate (V), titanium trichloride, tungsten (VI) oxide and sodium phosphate can be used in oxidation reaction (refer to Patent Literature 1 and Non-patent Literatures 1-3, for example).

Meanwhile, as the method for producing the corresponding cyclic phenol sulfide, there are the method which comprises the steps of using a phenol compound, sulfur and an alkali metal reagent as raw materials and synthesizing them by heating (refer to Patent Literatures 2-4, and Non-patent Literature 4, for example), and the method which comprises the steps of using a chain phenol sulfide, sulfur and an alkali metal reagent as raw materials and synthesizing them by heating (refer to Patent Literatures 5-8, for example). In each case, the produced cyclic phenol sulfide is isolated by processes such as crystallization, filtration, purification and drying.

Therefore, when producing an oxidized cyclic phenol sulfide, a cyclic phenol sulfide is once taken as the intermediate, and then it is again poured in a reactor, and a reaction reagent(s) is added thereto to conduct the oxidation reaction and to produce an oxidized cyclic phenol sulfide.

In the method for producing a cyclic phenol sulfide which comprises the steps of using a phenol compound, sulfur and an alkali metal reagent as raw materials and synthesizing them by heating, thermal cost is high since the reaction is conducted at high temperature. Further, the method requires equipments for safely detoxifying byproduct hydrogen sulfide gas. In addition, isolation of a cyclic phenol sulfide by processes such as crystallization, filtration, purification and drying causes loss of products in each treatment process, and it also causes the decrease in work efficiency due to the increase in operation time. Thus, it is costly to produce a cyclic phenol sulfide, and it makes a cyclic phenol sulfide expensive. Consequently, the production cost of an oxidized cyclic phenol sulfide which is the end product is much higher. It has been expected to find, as an effective cost improvement plan, a method for producing an oxidized cyclic phenol sulfide which comprises the steps of producing a cyclic phenol sulfide in the first reaction, and conducting thereto oxidation reaction which is the second reaction, without requiring various processes before said next reaction process and without various materials required for conducting the various processes together with improving work efficiency.

Patent Literature 1: WO 98/09959
Patent Literature 2: JP 9-227553 A
Patent Literature 3: JP 10-081681 A
Patent Literature 4: JP 2002-193963 A
Patent Literature 5: JP 10-081680 A
Patent Literature 6: JP 11-049770 A
Patent Literature 7: JP 2000-273096 A
Patent Literature 8: JP 2002-255961 A
Non-patent Literature 1: TETRAHEDRON LETTERS 39 (1998) 7559-7562
Non-patent Literature 2: TETRAHEDRON 57 (2001) 5557-5563
Non-patent Literature 3: J. Chem. Soc., Chem. Commun., 1998, 1345
Non-patent Literature 4: H. Kumagai et al., Tetrahedron Lett. (1997), 38, 3971-3972

DISCLOSURE OF THE INVENTION

The object of the present invention is, in the method for producing an oxidized cyclic phenol sulfide, to provide a method for continuously producing an oxidized cyclic phenol sulfide which comprises the steps of producing a cyclic phenol sulfide in the first reaction (the first step) and, without taking the cyclic phenol sulfide out of a reactor, thereby continuously oxidizing it with an oxidizing agent in the same reactor as that of the first step (the second step).

The additional object of the present invention is to obtain a high-quality oxidized cyclic phenol sulfide in high yields.

The inventors have thoroughly studied to solve the above problems and found a method for continuously producing a high-quality oxidized cyclic phenol sulfide in high yields, and said method comprising the two continuous steps of using a phenol compound of the formula (1) as a raw material:

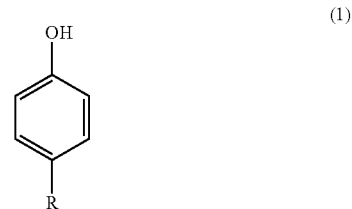

(1)

wherein R represents a straight or branched alkyl group having 1 to 6 carbon atoms,
and obtaining a cyclic phenol sulfide of the formula (2) (the first step):

(2)

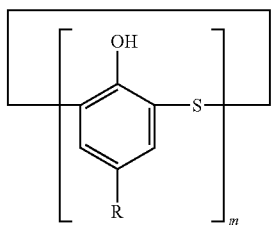

wherein R represents a straight or branched alkyl group having 1 to 6 carbon atoms, and m is an integer from 4 to 8; and without taking the obtained cyclic phenol sulfide out of a reactor, oxidizing it with an oxidizing agent(s) to obtain an oxidized cyclic phenol sulfide of the formula (3) (the second step):

(3)

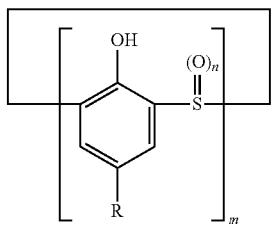

wherein R represents a straight or branched alkyl group having 1 to 6 carbon atoms, m is an integer from 4 to 8, and n is 1 or 2.

According to the continuous production method of the present invention, it needs neither various processes required before transferring a cyclic phenol sulfide produced in the first reaction to the next step nor various materials required for conducting the various processes. In addition, by continuously conducting the second step, i.e. oxidation reaction to produce an oxidized cyclic phenol sulfide, it becomes possible to obtain an oxidized cyclic phenol sulfide which is the end product high in both quality and yields, and to drastically decrease the production cost thereof. Therefore, the continuous production method of the present invention is an excellent industrial production method.

BEST MODE FOR CARRYING OUT THE INVENTION

In a phenol compound of the formula (1) which is a raw material in the first step of the present invention, examples of a straight or branched alkyl group having 1 to 6 carbon atoms represented by R in the formula (1) include following groups: a methyl group, ethyl group, n-propyl group, 2-propyl group, n-butyl group, sec-butyl group, 2-methylpropyl group, tert-butyl group, n-pentyl group, 1-methylbutyl group, 1-ethylpropyl group, 1,1-dimethylpropyl group, 1,2-dimethylpropyl group, n-hexyl group, 1-methylpentyl group, 2-methylpentyl group, 3-methylpentyl group, 4-methylpentyl group, 1-ethyl-butyl group, 2-ethylbutyl group, 1,1-dimethylbutyl group, 1,2-dimethylbutyl group, 1,3-dimethylbutyl group, 1,4-dimethylbutyl group, 2,2-dimethylbutyl group, 2,3-dimethylbutyl group, 3,3-dimethylbutyl group, 1-ethyl-2-methyl-propyl group, and 1,1,2-trimethylpropyl group.

In an oxidized phenol sulfide of the formula (3) of the present invention, n is 1 or 2, and n of S=(O)n group in each molecule may be the same or different from each other, and it is preferable that each molecule satisfies $1.5 \, m \leq N \leq 2 \, m$ when defining a total of n as N. The further preferable range of N is $1.7 \, m \leq N \leq 2m$.

Next, the first step of the present invention: the method for producing a cyclic phenol sulfide is illustrated. In the method for producing a cyclic phenol sulfide which is the first step of the present invention, it is preferable that the cyclizing reaction is conducted in the presence of a solvent(s). The preferable usage amount of the solvent(s) is 0.1 to 1 L and more preferably 0.3 to 0.6 L per 1 mol of a phenol compound of the formula (1) which is a raw material. The kind of the solvents includes saturated aliphatic ethers, aromatic ethers, saturated aliphatic thioethers, aromatic thioethers, saturated aliphatic hydrocarbons, and aromatic hydrocarbons. Aromatic ethers, aromatic thioethers and aromatic hydrocarbons are preferable among them, and diphenyl ether is particularly preferable.

In the first step of the present invention, the feed molar ratio of sulfur to a phenol compound of the formula (1) is preferably 1.7 to 2.5 molar equivalent of sulfur to 1 mol of the phenol compound, and particularly preferably 1.9 to 2.1 molar equivalent thereof.

In the first step of the present invention, various alkali metal reagents such as alkali metals, hydrogenated alkali metals, carbonic alkali metals and alkali metal alkoxides are usable in the cyclizing reaction, and alkali metal hydroxides are preferable. Examples of alkali metal hydroxides include lithium hydroxide, sodium hydroxide, and potassium hydroxide. Sodium hydroxide is particularly preferable.

The preferable usage amount of an alkali metal reagent is 0.25 to 0.75 molar equivalent and particularly preferably 0.4 to 0.6 molar equivalent per 1 mol of a phenol compound of the formula (1).

In the first step of the present invention, it is preferable that the cyclizing reaction is conducted under an inactive gas atmosphere, and it is further preferable that the reaction is conducted while introducing an inactive gas into the reaction system. Examples of the inactive gas include nitrogen, helium and argon, and the kind thereof is not particularly limited in practicing the present invention.

In the first step of the present invention, the production is conducted while removing water and hydrogen sulfide each of which is generated in the cyclizing reaction. The generated water and hydrogen sulfide are removed from the system by introducing an inactive gas into the system or by the suction under slightly reduced pressure without boiling a solvent(s). Then, they are continuously captured by being absorbed into an alkaline aqueous solution such as an aqueous solution of sodium hydroxide or an amine solution such as ethanolamine; or by being adsorbed on activated carbon, molecular sieve, iron oxide, zinc oxide, or the like.

In the first step of the present invention, it is preferable that the reaction temperature of the cyclizing reaction is risen in three steps. Though the intended compound can be obtained by rising the temperature to the final reaction temperature in one step, it induces the decrease in the yield thereof. Thus, it is preferable to rise the temperature in three steps. Namely, the reaction temperature is heated up to 120 to 140° C. (the first step) and kept in the same temperature for 0.5 hour or more. Though there is no upper limit of the reaction time thereof, 0.5 to 8 hours is preferable since more than that increases the production cost. Subsequently, the reaction temperature is heated up to 160 to 180° C. (the second step) and kept in the same temperature for 0.5 hour or more. Though there is no upper limit of the reaction time thereof, 0.5 to 8 hours is preferable since more than that increases the production cost. Finally, the reaction temperature is heated up to 210° C. or higher (the third step). When the reaction temperature herein is 200° C. or higher, a cyclic quatromer produces. However, in order to produce a number of more macrocyclic cyclic phenol sulfides wherein m=5 to 9 in the formula (2), it is preferable to rise the reaction temperature to 210° C. or higher. Though there is no upper limit of the reaction temperature, 250° C. or lower is preferable since more than that increases the production cost. Though the reaction time changes depending on the reaction temperature and the kind of a phenol compound which is a raw material, it is preferable to set the time to 1 to 30 hours.

The reaction mixture can be used to the next step without conducting an additional step(s). It is also possible to use the reaction mixture to the second step after removing remnant hydrogen sulfide by suction under slightly reduced pressure with an aspirator or the like, or by introducing nitrogen gas.

Next, the second step of the present invention: the method for producing an oxidized cyclic phenol sulfide is illustrated. In the method for producing an oxidized cyclic phenol sulfide which is the second step of the present invention, an oxidizing agent(s) is directly added to the reactor after completion of the first step, wherein the reaction mixture of a cyclic phenol sulfide of the formula (2) obtained in the first step is not taken out of the reactor. Namely, it is preferable to continuously transfer the reaction mixture after completion of the first step to the second step in the same reactor without conducting an additional step(s) thereto and without taking it out of the reactor.

After completion of the first step, upon transferring the reaction mixture to the second step, it is preferable to cool down the reaction system in the first step to 50-90° C., and more preferably 60-80° C. Cooling down can be conducted by any cooling method.

In the second step of the present invention, it is preferable that an organic carboxylic acid is used as a solvent used in the oxidation reaction. Examples thereof include an acetic acid, a propionic acid and a butyric acid, and an acetic acid is particularly preferable. According to the production method of the present invention, there is an advantage that oxidation proceeds even in the state where the cyclic phenol sulfide of the formula (2), which is a raw material, is dispersed in a solvent(s). Thus, there is no need to use an extra amount of a solvent for preparing a solution state, and the reaction can be conducted in 0.1 or more and less than 12 parts by weight of an organic carboxylic acid per 1 part by weight of the phenol compound of the formula (1). 0.2 to 8.4 parts by weight thereof is preferable, and 0.6 to 6 parts by weight thereof is more preferable.

In the second step of the present invention, various oxidizing agents can be used as the oxidizing agent used in the oxidation reaction, e.g., hydrogen peroxide, sodium perborate, sodium perchlorate, and an m-chloroperbenzoic acid. Hydrogen peroxide water is preferable among them, and 35% hydrogen peroxide water is more preferable from the viewpoint of safe handling.

The usage amount of hydrogen peroxide is preferably 1 to 6 moles per 1 mol of the phenol compound of the formula (1) and particularly preferably 2 to 4 moles.

In the second step of the present invention, the oxidation reaction can be promoted by making a metal catalyst(s) coexist during the reaction. It is possible to use various metal catalysts such as vanadium (V) oxide, sodium metavanadate (V), tungsten (VI) oxide and sodium phosphate and cobalt acetate. A tungsten acid and sodium tungstate are preferable, and sodium tungstate is particularly preferable. The usage amount thereof is preferably 0.0025 to 10 mol % per 1 mol of the phenol compound of the formula (1), and particularly preferably 2.5 to 5 mol %.

The reaction rate can be increased without affecting the reaction composition by adding metal carboxylate in advance or during the reaction in addition to a metal catalyst(s). A preferable example of metal carboxylate which is a reaction accelerator is metal acetate, and sodium acetate is particularly preferable. The usage amount thereof is preferably 0.01 to 5 moles per 1 mol of a metal catalyst and more preferably 1 to 2.5 moles.

In the second step of the present invention, the oxidation reaction can be promoted by making a phase-transfer catalyst(s) coexist during the reaction. Various phase-transfer catalysts can be used, and it is preferable to use tetraalkylammonium salts such as tetrabutylammonium salicylate, tetraethylammonium p-toluenesulfonate and tetrabutylammonium perchlorate. Tetrabutylammonium hydrogen sulphate is particularly preferable. The usage amount thereof is preferably 0.025 to 5 mol % per 1 mol of the phenol compound of the formula (1), and particularly preferably 1.25 to 2.5 mol %. By making a phase-transfer catalyst(s) coexist, not only the oxidation reaction can be promoted, but also the oxidation reaction can be conducted in fewer usage amounts of the organic carboxylic acid. An alkyl group in tetraalkylammonium salts preferably has 1-6 carbon atoms and more preferably 1-4 carbon atoms.

In the second step of the present invention, when using hydrogen peroxide as an oxidizing agent, it is preferable that hydrogen peroxide water is added dropwise under heating to a mixture comprising the cyclic phenol sulfide of the formula (2), a solvent, a catalyst and a reaction accelerator. Though it is possible to previously pour a total amount of hydrogen peroxide water together with the mixture and proceed with the reaction, it is particularly preferable to add it dropwise for safety. In the second step of the present invention, the start temperature of hydrogen peroxide oxidation is about 60-70° C. When the temperature is lower than 60° C., hydrogen peroxide accumulates and it carries runaway risk when heating. Therefore, in order to start oxidation safely and smoothly, it is preferable that the reaction mixture is previously heated up to 60-70° C. and then hydrogen peroxide water is added dropwise thereto. Though this oxidation reaction is exothermic reaction and heat evolution is especially seen at the beginning of the reaction, the method of the present invention has an advantage of controlling heat evolution by controlling the drop rate of hydrogen peroxide. Basically, when and after adding dropwise hydrogen peroxide water in an amount of 2 moles per 1 mol of the phenol compound of the formula (1), heat evolution is hardly seen. Though the drop time is not particularly limited, it is preferably 0.5 to 10 hours, and particularly preferably 1 to 7 hours. After the drop of an oxidizing agent (hydrogen peroxide water) is completed, the reaction mixture is continuously stirred at 60-90° C. for 1 to 24 hours to complete the reaction.

Since the reaction quantitatively proceeds, though the oxidation reaction mixture exists in a solvent in dispersion state, it is cooled down to appropriate temperature after the completion of the reaction, and, without any complicated treatment step, it is just filtered and washed to easily separate and obtain only a reaction product from the reaction mixture. Thus, an amount of the solvent used for the reaction can be drastically decreased. Though the cooling temperature is not particularly limited, it is preferable to cool down the mixture to room temperature.

In the oxidation reaction of the second step of the present invention, by using one or more kinds selected from the groups of organic carboxylic acids, metal catalysts and phase-transfer catalysts, it is possible to adjust the content of an oxidized cyclic phenol sulfide wherein n=2 in the oxidized cyclic phenol sulfide of the formula (3).

When using the reaction product of the present invention as a static charge control agent, it is preferable to add the step of adding 0.0025 to 2.5 moles of a mineral acid, and more preferably 0.5 to 1 moles thereof per 1 mol of the cyclic phenol sulfide of the formula (1) in the same reactor at the end of the oxidation reaction of the second step. Though the temperature and time when adding a mineral acid are not particularly limited, it is preferable to add a mineral acid for 1 hour at 60-90° C. which is the same temperature as the final temperature in the oxidation reaction. Since a part of the oxidized cyclic phenol sulfide of the formula (3) which is the reaction product remains as metal phenolate, the object of this treatment with a mineral acid is to neutralize metal phenolate and decrease a content of metal salts of impurities in the oxidation product. In the case of not treating with a mineral acid, metal residual volume in the oxidized cyclic phenol sulfide of the formula (3) is beyond 1000 ppm and, therefore, decreased charging performance is seen. On the other hand, in the case of treating with a mineral acid, metal residual volume is limited to 1000 ppm or less and, therefore, it is possible to obtain an oxidized cyclic phenol sulfide of which charging performance is not decreased. Examples of used mineral acids include a hydrochloric acid, a sulfuric acid, a nitric acid, a phosphoric acid, and a boric acid. Though a used mineral acid is not particularly limited, a hydrochloric acid and a sulfuric acid are preferable, and a hydrochloric acid is more preferable since inorganic salts which are produced by neutralization are easily removed when filtering and washing.

EXAMPLE 1

Next, Examples will further illustrate the present invention. They only explain the present invention and do not particularly limit the invention.

The purity and relative proportions of an oxidized cyclic phenol sulfide of the formula (3) produced by the method of the present invention and those of a cyclic phenol sulfide of the formula (2) which is the intermediate product were analyzed by a high-performance liquid chromatography (herein after referred to as HPLC). The measurement condition of HPLC for analyzing the cyclic phenol sulfide is as follows: device: LC-6A by Shimadzu Corporation; column: Develosil ODS-HG-5 (inside diameter 4.6 mm, column length 250 mm) by Nomura Chemical Co., Ltd.; column temperature: 40° C.; mobile phase: tetrahydrofuran/acetonitrile/water/trifluoroacetic acid=450/400/150/2 (v/v/v/v); current speed: 1.0 mL/min.; filling amount: 1 μL; and concentration of a sample: 1000 ppm. Further, the measurement condition of HPLC for analyzing the oxidized cyclic phenol sulfide is as follows: LC-6A by Shimadzu Corporation; column: Develosil ODS-HG-5 (inside diameter 4.6 mm, column length 250 mm) by Nomura Chemical Co., Ltd.; column temperature: 40° C.; mobile phase: tetrahydrofuran/acetonitrile/water/trifluoroacetic acid=350/350/300/2 (v/v/v/v); current speed: 1.0 mL/min.; filling amount: 1 μL; and concentration of a sample: 1000 ppm. Further, the sodium content in the oxidized cyclic phenol sulfide of the formula (3) produced by the method of the present invention was measured by fluorescent X-ray analysis. The measurement was conducted as follows. The oxidized cyclic phenol sulfide was solidified by being pressed to formulate it into a disk shape of 40-50 mm in diameter and 3 mm thick. Then, it was measured with a fluorescent X-ray spectrometer (PW2400 produced by Philips).

60.1 g (0.4 mol) of 4-tert-butylphenol, 25.6 g of sulfur (twofold mol per 1 mol of 4-tert-butylphenol) and 8.0 g of sodium hydroxide (a half mol per 1 mol of 4-tert-butylphenol) were poured in a 500 mL four-neck flask with a mixer, a cooling tube, a thermometer and a gas-introducing tube. 180.3 g of diphenyl ether was added thereto and heated up to 130° C. with stirring the mixture in the current of nitrogen gas. The reaction was conducted for 0.5 hour at 130° C. Then, the temperature was risen to 170° C., and the reaction was conducted for 0.5 hour at 170° C. Finally, after heating the mixture up to 230° C., the reaction was conducted for 12 hours at 230° C. The above reactions were conducted removing generated water and hydrogen sulfide by the method comprising the steps of letting nitrogen into the reactor and pushing water and hydrogen sulfide out to the system; and contacting them to an aqueous solution of sodium hydroxide to absorb them.

The obtained reaction mixture comprising a cyclic phenol sulfide was cooled down to 70° C. Then, 72 g of an acetic acid and 6.6 g (0.02 mol) of sodium tungstate dehydrate were added thereto, and 150 g (1.54 mol) of 35% hydrogen peroxide water was added dropwise to the flask with stirring for 1.5 hours with a drip funnel. After stirring the mixture at 70° C. for 15 hours, 20.3 g of 36% hydrochloric acid was added thereto and further stirred for 1 hour, and cooled down to room temperature. The obtained product was filtered under reduced pressure, washed with 100 mL of water, 100 mL of toluene twice, and lastly 100 mL of water, and vacuum dried for 24 hours at 80° C. to obtain 65.2 g (yield 77%) of an oxidized cyclic phenol sulfide.

The relative proportions of the obtained oxidized cyclic phenol sulfide by HPLC analysis were as follows: the oxidized cyclic quatromer indicated the peak area ratio of 62.2%; the oxidized cyclic octamer indicated the peak area ratio of 5.8%; and the partially-oxidized form of an oxidized cyclic quatromer indicated the peak area ratio of 32.0%. It took 3 days to produce the oxidized cyclic phenol sulfide.

Further, the sodium content in the obtained oxidized cyclic phenol sulfide was 731 ppm.

EXAMPLE 2

36.1 g (0.24 mol) of 4-tert-butylphenol, 15.4 g of sulfur (twofold mol per 1 mol of 4-tert-butylphenol) and 4.8 g of sodium hydroxide (a half mol per 1 mol of 4-tert-butylphenol) were poured in a 300 mL four-neck flask with a mixer, a cooling tube, a thermometer and a gas-introducing tube. 108.2 g of diphenyl ether was added thereto and heated up to 130° C. with stirring the mixture in the current of nitrogen gas. The reaction was conducted for 0.5 hour at 130° C. Then, the temperature was risen to 170° C., and the reaction was conducted for 0.5 hour at 170° C. Finally, after heating the mixture up to 250° C., the reaction was conducted for 6 hours at 250° C. The above reactions were conducted removing generated water and hydrogen sulfide by the method comprising the steps of letting nitrogen into the reactor and pushing water and hydrogen sulfide out to the system; and contacting them to an aqueous solution of sodium hydroxide to absorb them.

The obtained reaction mixture comprising a cyclic phenol sulfide was cooled down to 70° C. Then, 43 g of an acetic acid and 3.96 g (0.012 mol) of sodium tungstate dehydrate were added thereto, and 101.8 g (1.05 mol) of 35% hydrogen peroxide water was added dropwise to the flask with stirring for 1.3 hours with a drip funnel. After stirring the mixture at 70° C. for 18 hours, 15.6 g of 36% hydrochloric acid was added thereto and further stirred for 1 hour, and cooled down to room temperature. The obtained product was filtered under reduced pressure, washed with 60 mL of water, 60 mL of toluene twice, and lastly 60 mL of water, and vacuum dried for 24 hours at 80° C. to obtain 42.6 g (yield 84%) of an oxidized cyclic phenol sulfide.

The relative proportions of the obtained oxidized cyclic phenol sulfide by HPLC analysis were as follows: the oxidized cyclic quatromer indicated the peak area ratio of 62.4%; the oxidized cyclic octamer indicated the peak area ratio of 6.2%; and the partially-oxidized form of an oxidized cyclic quatromer indicated the peak area ratio of 31.1%. It took 3 days to produce the oxidized cyclic phenol sulfide.

Further, the sodium content in the obtained oxidized cyclic phenol sulfide was 765 ppm.

EXAMPLE 3

The reaction was conducted in the same condition as that of Example 1, except that 13.2 g (0.04 mol) of sodium tungstate dehydrate was added to the reaction mixture. As a result, 59.8 g (yield 70%) of an oxidized cyclic phenol sulfide was obtained.

The relative proportions of the obtained oxidized cyclic phenol sulfide by HPLC analysis were as follows: the oxidized cyclic quatromer indicated the peak area ratio of 64.0%; the oxidized cyclic octamer indicated the peak area ratio of 7.0%; and the partially-oxidized form of an oxidized cyclic quatromer indicated the peak area ratio of 29.0%. It took 3 days to produce the oxidized cyclic phenol sulfide.

Further, the sodium content in the obtained oxidized cyclic phenol sulfide was 689 ppm.

EXAMPLE 4

The reaction was conducted in the same condition as that of Example 2, except that 87 g of an acetic acid was added to the reaction mixture. As a result, 39.5 g (yield 78%) of an oxidized cyclic phenol sulfide was obtained.

The relative proportions of the obtained oxidized cyclic phenol sulfide by HPLC analysis were as follows: the oxidized cyclic quatromer indicated the peak area ratio of 80.1%; the oxidized cyclic octamer indicated the peak area ratio of 7.2%; and the partially-oxidized form of an oxidized cyclic quatromer indicated the peak area ratio of 12.7%. It took 3 days to produce the oxidized cyclic phenol sulfide.

Further, the sodium content in the obtained oxidized cyclic phenol sulfide was 613 ppm.

EXAMPLE 5

The reaction was conducted in the same condition as that of Example 2, except that 130 g of an acetic acid was added to the reaction mixture. As a result, 38.9 g (yield 76%) of an oxidized cyclic phenol sulfide was obtained.

The relative proportions of the obtained oxidized cyclic phenol sulfide by HPLC analysis were as follows: the oxidized cyclic quatromer indicated the peak area ratio of 90.7%; the oxidized cyclic octamer indicated the peak area ratio of 6.8%; and the partially-oxidized form of an oxidized cyclic quatromer indicated the peak area ratio of 2.5%. It took 3 days to produce the oxidized cyclic phenol sulfide.

Further, the sodium content in the obtained oxidized cyclic phenol sulfide was 541 ppm.

EXAMPLE 6

The reaction was conducted in the same condition as that of Example 2, except that 173 g of an acetic acid was added to the reaction mixture. As a result, 37.6 g (yield 74%) of an oxidized cyclic phenol sulfide was obtained.

The relative proportions of the obtained oxidized cyclic phenol sulfide by HPLC analysis were as follows: the oxidized cyclic quatromer indicated the peak area ratio of 92.2%; the oxidized cyclic octamer indicated the peak area ratio of 6.5%; and the partially-oxidized form of an oxidized cyclic quatromer indicated the peak area ratio of 1.3%. It took 3 days to produce the oxidized cyclic phenol sulfide.

Further, the sodium content in the obtained oxidized cyclic phenol sulfide was 484 ppm.

EXAMPLE 7

The reaction was conducted in the same condition as that of Example 1, except that 72 g of an acetic acid and 6.6 g (0.02 mol) of sodium tungstate dehydrate were added to the reaction mixture; and 3.4 g (0.01 mol) of tetrabutylammonium hydrogen sulphate was further added thereto. As a result, 59.3 g (yield 70%) of an oxidized cyclic phenol sulfide was obtained.

The relative proportions of the obtained oxidized cyclic phenol sulfide by HPLC analysis were as follows: the oxidized cyclic quatromer indicated the peak area ratio of 94.2%; the oxidized cyclic octamer indicated the peak area ratio of 6.8%; and the partially-oxidized form of an oxidized cyclic quatromer was not able to be detected. It took 3 days to produce the oxidized cyclic phenol sulfide.

Further, the sodium content in the obtained oxidized cyclic phenol sulfide was 211 ppm.

COMPARATIVE EXAMPLE 1

60.1 g (0.4 mol) of 4-tert-butylphenol, 25.6 g of sulfur (twofold mol per 1 mol of 4-tert-butylphenol) and 8.0 g of sodium hydroxide (a half mol per 1 mol of 4-tert-butylphenol) were poured in a 500 mL four-neck flask with a mixer, a cooling tube, a thermometer and a gas-introducing tube. 180.3 g of diphenyl ether was added thereto and heated up to 130° C. with stirring the mixture in the current of nitrogen gas. The reaction was conducted for 0.5 hour at 130° C. Then, the temperature was risen to 170° C., and the reaction was conducted for 0.5 hour at 170° C. Finally, after heating the mixture up to 230° C., the reaction was conducted for 12 hours at 230° C. The above reactions were conducted removing generated water and hydrogen sulfide by the method comprising the steps of letting nitrogen into the reactor and pushing water and hydrogen sulfide out to the system; and contacting them to an aqueous solution of sodium hydroxide to absorb them.

The reaction mixture was cooled down to room temperature and neutralized by adding 40 mL of an aqueous solution of 3 mol/L sulfuric acid thereto. Then, 100 mL of a mixed solvent of isopropyl alcohol/water (88/12, v/v) was added thereto to precipitate crystals. The obtained crystals were filtered, washed with 100 mL of a mixed solvent of isopropyl alcohol/water (88/12, v/v), 120 mL of water twice, and lastly 100 mL of a mixed solvent of isopropyl alcohol/water (88/12, v/v), and vacuum dried at 120° C. overnight to obtain 56.6 g (yield 79%) of a cyclic phenol sulfide.

56.2 g (0.078 mol) of the obtained cyclic phenol sulfide, 224.8 g (fourfold wt/wt) of an acetic acid, 5.15 g (0.0156 mol) of sodium tungstate dehydrate and 5.31 g (0.039 mol) of sodium acetate trihydrate were poured in a 500 mL four-neck flask with a mixer, a cooling tube and a thermometer, and heated up to 60° C. with stirring. 121.2 g (1.248 mol) of 35% hydrogen peroxide water was added dropwise to the flask for about 1.5 hours with a drip funnel. After stirring the mixture for 15 hours at 70° C., 15.8 g of 36% hydrochloric acid was added thereto and further stirred for 1 hour, and cooled down to room temperature. The obtained product was filtered under reduced pressure, washed with 80 mL of water three times, and vacuum dried for 24 hours at 80° C. to obtain 58.3 g (yield 88%) of an oxidized cyclic phenol sulfide.

The relative proportions of the obtained oxidized cyclic phenol sulfide by HPLC analysis were as follows: the oxidized cyclic quatromer indicated the peak area ratio of 89.1%; the oxidized cyclic octamer indicated the peak area ratio of 5.7%; and the partially-oxidized form of an oxidized cyclic quatromer indicated the peak area ratio of 1.4%. The total yield from 4-tert-butylphenol is 69%, which is a low value. It took 4 days to produce the oxidized cyclic phenol sulfide, and a total amount of used solvents was 50% or more than that of the solvents used in the production method of the present invention.

Further, the sodium content in the obtained oxidized cyclic phenol sulfide was 551 ppm.

According to the method for continuously producing an oxidized cyclic phenol sulfide of the present invention, there is an advantage that a cyclic phenol sulfide produced in the first cyclizing reaction (the first step) can be, without taking it out of the reactor, continuously oxidized with an oxidizing agent (the second step) to produce an oxidized cyclic phenol sulfide. Namely, since the production time can be shortened and materials required for taking the cyclic phenol sulfide out of the reactor are unnecessary, it is possible to easily produce the oxidized cyclic phenol sulfide of the formula (3) in high yields with decreasing a content of impurities, and together with improving productive efficiency and lowering costs as compared to prior arts.

What is claimed is:

1. A method for continuously producing an oxidized cyclic phenol sulfide which comprises the continuous steps of reacting a phenol compound of the following formula (1) as a raw material with 1.7 to 2.5 molar equivalent of sulfur and 0.25 to 0.75 molar equivalent of an alkali metal reagent per 1 mol of the phenol compound (the first step);

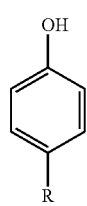

(1)

wherein R represents a straight or branched alkyl group having 1 to 6 carbon atoms, and oxidizing a cyclic phenol sulfide of the following formula (2) produced by the above reaction with an oxidizing agent(s) in the same reactor as that of the first step and without taking the cyclic phenol sulfide out of the reactor;

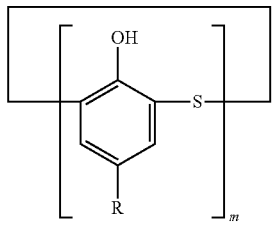

(2)

wherein R represents a straight or branched alkyl group having 1 to 6 carbon atoms, and m is an integer from 4 to 8, to obtain an oxidized cyclic phenol sulfide of the following formula (3) (the second step):

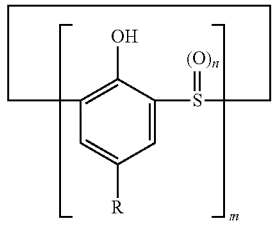

(3)

wherein R represents a straight or branched alkyl group having 1 to 6 carbon atoms, m is an integer from 4 to 8, and n is 1 or 2.

2. The method for continuously producing the oxidized cyclic phenol sulfide according to claim 1 which further comprises the step of removing water and hydrogen sulfide generated in the first step out of the reactor.

3. The method for continuously producing the oxidized cyclic phenol sulfide according to claim 1, wherein, upon transfer to the second step after the completion of the first step, the temperature of the reaction system in the first step is cooled down to 50-90° C.

4. The method for continuously producing the oxidized cyclic phenol sulfide according to claim 1, wherein, in the formula (3), n of S=(O)n group in each molecule may be the same or different from each other, and each molecule satisfies $1.5m \leq N \leq 2m$ when defining a total of n as N.

5. The method for continuously producing the oxidized cyclic phenol sulfide according to claim 4, wherein, in the second step, 1 to 6 moles of hydrogen peroxide per 1 mol of the phenol compound of the formula (1) is acted as an oxidizing agent.

6. The method for continuously producing the oxidized cyclic phenol sulfide according to claim 5, wherein, when oxidizing the cyclic phenol sulfide of the formula (2) with an oxidizing agent in the second step, the oxidization is conducted in the presence of 0.1 to 12 parts by weight of an organic carboxylic acid per 1 part by weight of the phenol compound of the formula (1).

7. The method for continuously producing the oxidized cyclic phenol sulfide according to claim 6, wherein, when oxidizing the cyclic phenol sulfide of the formula (2) with an oxidizing agent in the second step, the oxidization is conducted in the presence of 0.0025 to 10 mol % of a metal catalyst per 1 mol of the phenol compound of the formula (1).

8. The method for continuously producing the oxidized cyclic phenol sulfide according to claim 7, wherein a tungsten acid or sodium tungstate is used as the metal catalyst, and 0.01 to 5 moles of metal organic carboxylate per 1 mol of the tungsten acid or the sodium tungstate is used.

9. The method for continuously producing the oxidized cyclic phenol sulfide according to claim 8, wherein, when oxidizing the cyclic phenol sulfide of the formula (2) with an oxidizing agent in the second step, the oxidization is conducted in the presence of 0.025 to 5 mol % of a phase-transfer catalyst per 1 mol of the phenol compound of the formula (1).

10. The method for continuously producing the oxidized cyclic phenol sulfide according to claim 9, wherein the phase-transfer catalyst is a tetraalkylammonium salt.

11. The method for continuously producing the oxidized cyclic phenol sulfide according to claim 1, wherein, when oxidizing the cyclic phenol sulfide of the formula (2) with an oxidizing agent in the second step, the content of an oxidized cyclic phenol sulfide wherein n =2 in the oxidized cyclic phenol sulfide of the formula (3) is adjusted by using one or more kinds selected from the groups of organic carboxylic acids, metal catalysts and phase-transfer catalysts.

12. The method for continuously producing the oxidized cyclic phenol sulfide according to claim 11 which further comprises, after the second step and after the completion of the oxidation reaction of the cyclic phenol sulfide of the formula (2), the step of treating with 0.0025 to 2.5 moles of a mineral acid per 1 mol of the phenol compound of the formula (1) in the same reactor as that of the second step.

13. The method for continuously producing the oxidized cyclic phenol sulfide according to claim 9 wherein the sodium content in the oxidized cyclic phenol sulfide of the formula (3) is 1000 ppm or less.

14. The method for continuously producing the oxidized cyclic phenol sulfide according to claim 12 wherein the sodium content in the oxidized cyclic phenol sulfide of the formula (3) is 1000 ppm or less.

* * * * *